(12) United States Patent
Iverson

(10) Patent No.: US 6,450,809 B1
(45) Date of Patent: Sep. 17, 2002

(54) VERTEX DENTAL MODEL ARTICULATOR

(76) Inventor: Corey B. Iverson, 1931 Bonnie Brae, Riverside, CA (US) 92506

( * ) Notice: Subject to any disclaimer, the term of this patent is extended or adjusted under 35 U.S.C. 154(b) by 0 days.

(21) Appl. No.: 09/838,027

(22) Filed: Apr. 18, 2001

(51) Int. Cl.[7] .............................................. A61C 11/00
(52) U.S. Cl. ........................................ 433/64; 433/57
(58) Field of Search .............................. 433/64, 57, 63, 433/65, 60

(56) References Cited

U.S. PATENT DOCUMENTS

| | | | | |
|---|---|---|---|---|
| 530,524 A | * | 12/1894 | Hitch | 433/63 |
| 2,535,146 A | * | 12/1950 | Lyons | 433/58 |
| 2,600,899 A | * | 6/1952 | McClain | 433/63 |
| 4,200,981 A | | 5/1980 | Fine | 433/60 |
| 4,378,929 A | | 4/1983 | Huffman | 249/124 |
| 4,382,787 A | | 5/1983 | Huffman | 433/64 |
| 4,449,930 A | | 5/1984 | Huffman | 433/64 |
| 4,481,162 A | | 11/1984 | Huffman | 264/334 |
| 4,494,934 A | | 1/1985 | Huffman | 433/213 |
| 4,533,323 A | | 8/1985 | Huffman | 433/60 |
| 4,548,581 A | | 10/1985 | Huffman | 433/64 |
| 4,734,033 A | | 3/1988 | Huffman | 433/60 |
| 4,797,097 A | * | 1/1989 | Cohn | 433/64 |
| 4,842,242 A | | 6/1989 | Huffman | 249/54 |
| 5,007,829 A | | 4/1991 | Farrell | 433/61 |
| 5,106,296 A | | 4/1992 | Varde | 433/54 |
| 5,425,636 A | * | 6/1995 | Ghim | 433/64 |
| 5,622,497 A | | 4/1997 | Cho | 433/60 |
| 5,743,733 A | | 4/1998 | Crossland | 433/57 |
| 5,769,634 A | | 6/1998 | Choi | 433/64 |

* cited by examiner

Primary Examiner—John J. Wilson
(74) Attorney, Agent, or Firm—A. M. Fernandez

(57) ABSTRACT

An improved ball-and-socket joint for use with dental model articulators of a vertex type comprising two brackets hinged together at one end and each connected at the other end by a ball-and-socket joint to a separate one of two stone plates bearing dental castings. The ball-and-socket joints have releasable mechanical means for affixing the ball in the socket after the plates have been aligned for bite and occlusal fit between the dental castings. Affixing the ball in a socket is achieved by mechanically adjusting the diameter of one relative to the other of the socket and the ball to create a friction force that affixes the ball in the socket. In one embodiment, the mechanical means comprises a C-clamp having a concave band with a cross-sectional diameter substantially equal to the ball diameter and a gap to allow the ball to be snap-fit into the C-clamp. A bolt through flanges at the ends of the C-clamp is used to reduce a gap between flanges, thereby increasing without limit the frictional clamping force on the ball. In another embodiment, the ball is inserted into a truncated spherical cavity formed on a stalk in four parts with gaps between the parts. The ball gaps permit the ball to be snap-fit into the spherical cavity serving as the socket for the joint. A bolt threaded through the bracket base and stalk that supports the ball is turned to drive it between the four parts in the socket, thereby spreading apart the four parts of the ball in the cavity to produce the necessary friction force between the ball and cavity wall to affix the ball in the socket.

3 Claims, 2 Drawing Sheets

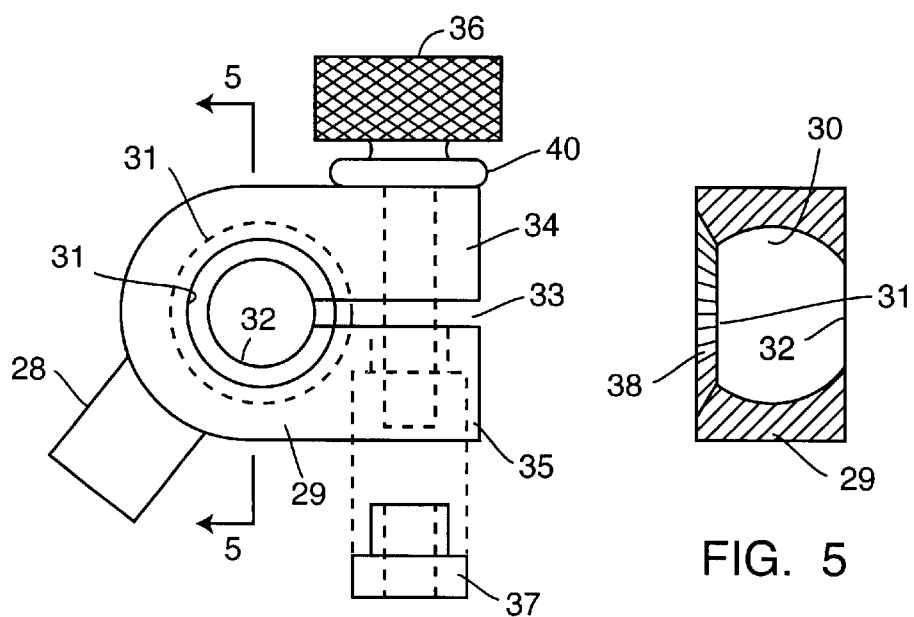
FIG. 4
FIG. 5
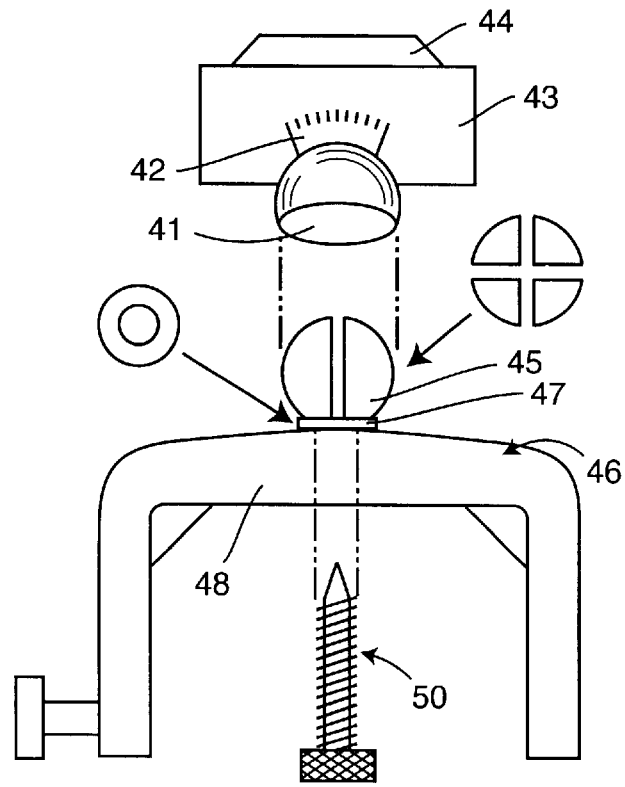
FIG. 6

VERTEX DENTAL MODEL ARTICULATOR

FIELD OF THE INVENTION

The present invention relates to dental model articulators of a vertex type disclosed in U.S. Pat. Nos. 4,382,787; 4,449,930; 4,533,323; 4,548,581 and 4,734,033.

BACKGROUND OF THE INVENTION

Dental articulators are widely used by dental laboratory technicians for holding and manipulating the dental castings of upper and lower sets of teeth while engaged in modeling dental prosthesis, such as a crown or a bridge for a missing tooth. Molds are first made of the patient's upper and lower set of teeth from which castings are then made, either integral with plates of casting stone material for holding them or separately. In either case, the dental castings are supported by a pair of stone plates that serve as upper and lower jaws hinged together through two U-shaped brackets as disclosed in the aforesaid prior-art patents, which by this reference are hereby incorporated herein. Together, the brackets emulate condyles for articulation of the lower jaw relative to the upper jaw and are used by the technician for initially adjusting the bite between the sets of teeth on the two plates and for continually checking occlusion between the teeth castings and the prosthesis during the process of modeling the prosthesis.

The pair of U-shaped brackets are hinged together at the ends of their two parallel arms to permit movement of one bracket relative to the other bracket about their hinge axis. The base between parallel arms of each bracket is connected to the rear face of a stone plate through a ball of a ball-and-socket joint which constitutes a vertex for the bracket. The socket for each joint is affixed on the back of its stone plate by a separate mounting means, while support for the ball on its bracket base is provided by a stalk slightly offset from the center of the bracket base such that, once the ball joint connection is completed, the centers of the balls supported on the hinged brackets lie on a common plane perpendicular to the axis of the hinged brackets and centered between the hinged bracket arms, as more fully described and illustrated in each of the aforesaid prior-art patents. By offsetting the ball of each bracket on its base in that manner, both brackets can be cast from the same mold, each with a hinge pin extending outwardly extending from one arm and a slotted perforation to receive a hinge pin in the other arm. Upon orienting one bracket 180° with respect to the other, the hinge pin of each may be snap-fit in the slotted perforation in an arm of the other bracket.

The sockets for the balls in the aforesaid prior-art patents are semispherical cavities which cannot hold the balls in their sockets while the dental castings are being initially aligned, much less during the modeling of the prosthesis. In order to provide a positive means for holding the balls in the cavities during initial alignment of the plates bearing the castings, curved fingers are provided that extend from the edges of the semispherical cavities over the balls. Each ball is snap-fit into its cavity past the fingers, but the clamping force of the fingers is insufficient to hold the balls in their position of initial alignment throughout the process of modeling the prosthesis. Consequently, it is necessary and sufficient to apply a fast setting glue, such as cynacrolate glue (commonly known as super glue) between the balls and the cavities after initial alignment. The importance of this glue in the prior-art patents referred to above is emphasized in the most recent U.S. Pat. No. 4,734,033. It shows a groove cast in the surfaces of each ball to facilitate flow of the glue into the cavity with the ball already in place. However, it is often necessary to realign the plates bearing the dental castings relative to each other during the process of modeling prosthesis. The use of glue to affix the ball in its socket then presents serious problems.

The problems arise from the need to remove the glue in order to free the bracket balls for realignment, which requires using a suitable solvent, such as acetate. This removal of glue is not only time consuming, but also dangerous because most solvents are highly volatile, flammable and toxic, particularly acetate, thus subjecting personnel in the dental laboratory to hazards that should be avoided. Moreover, the ball joints must stand in the solvent for a considerable time in order to fully dissolve the glue, which aggravates the risk of exposure not only to the toxicity of the solvent but also to the risk of fire or explosion in the laboratory. It would be preferable to use releasable mechanical means to affix the balls in the sockets, but previous attempts to accomplish that have not been successful.

One attempt has been to mechanically affix a ball in a socket using a set screw through one side of the socket to press the ball against the other side, thus clamping the ball between one point of contact set by the screw to force the ball in tangential contact with the socket wall on the opposite side of the ball. (See U.S. Pat. Nos. 4,797,097 and 5,007,829.) The frictional clamp created in that manner at two opposite points to the ball is not sufficient to prevent the ball from turning freely on an axis between those two points since tangential contact of the ball's spherical surface with any surface of the clamp, flat or curved, is but a point of contact, unless a curved surface is provided for the clamp with a radius of curvature that matches the radius of the ball with precision. Unless that radius of curvature is so matched, the area of contact with the ball is but a virtual joint. Only extreme pressure of the ball against the clamping surface can change that by increasing the area of contact either by deforming the ball or the clamping surface to more precisely conform the curvature of one to that of the other over a significant area around the point directly opposite the set screw.

Another prior-art approach utilizes a clam-type socket clamp, as shown in U.S. Pat. No. 5,106,296. There a ball is set between opposing cavities that form the clam-type socket. A locking screw through extensions of the opposing cantilevered cavities forces the cavities against the ball. Regardless of how tight the screw is turned, the clamping force of the two opposing cavities against the ball will not produce sufficient frictional force to affix the ball because each of the opposing cavities only makes tangential contact with the ball, which can then turn on an axis between the contact points. (See also U.S. Pat. No. 4,200,981.) For any clamping that will affix the orientation of the ball in the socket, the radius of curvature for the cavities of the clam-type socket must be made to match the radius of the ball with precision, and the gap between the two opposite cavities clamping the ball must be sufficient to allow for increasing the pressure of the cavities against the ball without limit. Thus, a clam-type socket would require precision in forming the cavities.

An object of this invention is to obviate the need for glue as a means for affixing ball-and-socket joints in a dental model articulator by instead utilizing releasable mechanical means for adjusting the relative diameters between the socket and the ball in a ball-and-socket joint in order to releasably affix the ball in the socket by frictional force that surrounds the ball over a significant area without the need for precision matching the radius of curvature of the socket cavity with the radius of the balls.

SUMMARY OF THE INVENTION

In accordance with a first embodiment of the present invention, the clamping friction between a ball and truncated spherical socket of a ball-and-socket joint in a dental model articulator is provided by a concave C-clamp that serves as the socket for releasably affixing the ball in the socket.

The C-clamp comprises a concave band around the spherical surface of the ball with the radius of concave curvature of the band substantially equal to the radius of the ball. Two free ends of the concave band that forms the C-clamp are each provided with a separate flange and a gap between the flanges. One flange is perforated and internally threaded to receive the end of a bolt, and the other flange is perforated to pass the threaded end of the bolt to the one flange internally threaded. After snap-fitting a ball into the C-clamp while the gap between the flanges is free to expand, the bolt is turned in one direction into the one internally threaded flange to close the gap between the flanges and produce sufficient tension in the concave band in order to firmly grip the ball within the C-clamp. Allowing the concave curvature of the band to mold itself to the ball as the C-clamp socket is put under tension obviates the need for any precision in matching the radius of concave curvature of the band to the radius of the ball.

The C-clamp socket for each articulator bracket ball is preferably made as an integral part of mounting means for affixing the C-clamp to the rear face of a dental plate so that the ball for each articulator bracket may then be formed as an integral part of the articulator bracket, but the reverse is equally effective and therefore is to be regarded as being equally within the scope of the appended claims.

In an alternative embodiment of the ball-and-socket joint, a truncated spherical cavity having a diameter substantially equal to the diameter of the ball serves as the socket for the ball-and-socket joint. The truncated spherical cavity is formed as an integral part of the mounting means with its opening for receiving the ball away from the mounting plate thereof.. The diameter of that opening is, of course, less than the diameter of the ball by a predetermined amount that allows inserting the ball in the cavity, as further described below. The ball is formed with a stalk as an integral part of an articulator bracket to support the ball on the base of the bracket between its two arms. The bracket base and stalk are both perforated and threaded to receive a bolt.

The ball formed on the stalk over the base of the bracket is divided into four equal parts, each separated by equal gaps. Each gap between any two adjacent parts is perpendicular to gaps between those same two parts and two other parts, with the intersecting gap spaces between the four corners of all the parts centered on the axis of the threaded perforation through and stalk and base. The threaded bolt through the stalk is selected to have a thread diameter greater than the space between diametrically opposite corners of the parts, such that as the threads of the bolt advance between the four corners of the parts, the four parts spread equally, thus pressing them against the wall of the truncated cavity to affix the ball in the socket by frictional force.

Upon initially press-fitting the ball into the socket through the slightly smaller opening of the truncated spherical socket, the four gapped parts of the ball, held in gapped position by the stalk, are bent slightly toward each other at their connection with the stalk while being inserted into the truncated cavity, thus effectively reducing the diameter of the ball while it is being inserted through the cavity opening. Once the gapped ball is inserted into the cavity, the bolt is turned to force its end through the threaded supporting base and stalk into the gapped ball between the four parts, thus forcing apart the four parts and thereby affixing the ball in the cavity. In that manner, the gaps between the four ball parts serve two purposes: to allow each of the four parts having a radius of curvature substantially at the stalk into the gaps between them, i.e., to bend toward each other, for insertion of the ball into the cavity; and to receive a bolt between the parts to force them against the cavity wall.

The novel features that are considered characteristic of this invention are set forth with particularity in the appended claims. The invention will best be understood from the following description when read in connection with the accompanying drawings.

BRIEF DESCRIPTION OF THE DRAWINGS

FIG. 4 is a plan view of a C-clamp socket for a ball-and-socket articulator of FIG. 1.

FIG. 5 is a cross section of the C-clamp socket taken on a line 4—4.

FIG. 6 illustrates a second embodiment of the present invention comprising a ball-and-socket arrangement for an articulator having an expandable ball for mechanically affixing the ball in a socket of an articulator by friction.

DETAILED DESCRIPTION OF THE INVENTION

Figure 1:
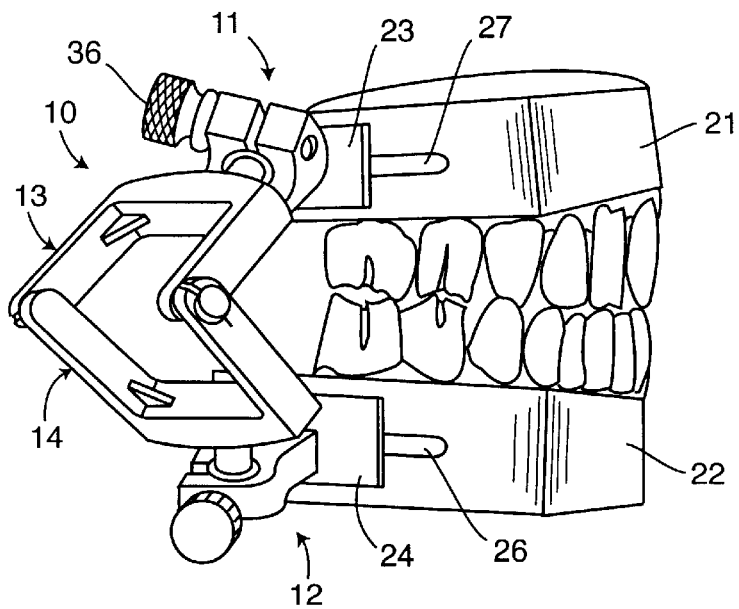
FIG. 1 illustrates an articulator having a novel ball-and-socket joint utilizing a friction C-clamp for the socket according to the present invention to hinge together stone plates bearing castings of a patient's teeth.
Figure 2:
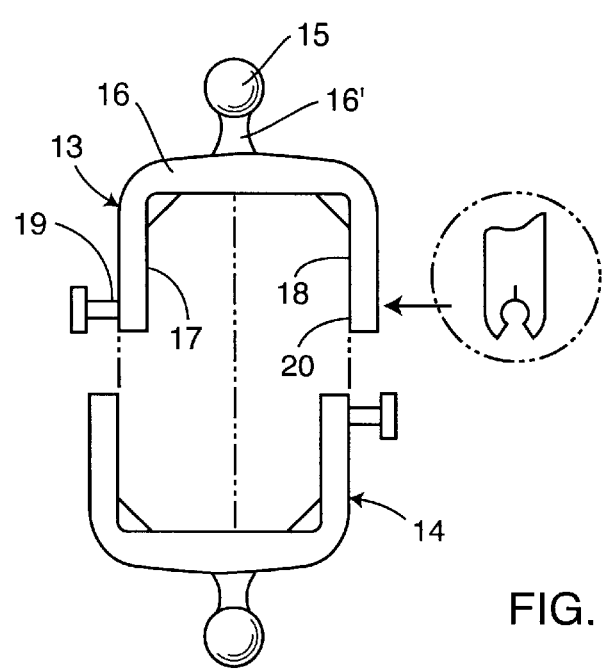
FIG. 2 is a plan view of a pair of brackets utilized in the articulator illustrated in FIG. 1.

Referring to FIG. 1, a vertex articulator 10 is shown with improved C-clamp ball-and-socket joints 11,12 and a pair of hinged U-shaped members or brackets 13,14. A plan view of each bracket is shown in FIG. 2. In practice each of the two brackets is cast in the same mold from flexible resilient plastic to have a ball 15 supported on a base 16 by a stalk 16' and two arms 17,18. One arm has a flanged pin 19 to receive a notched end 20 of the other hinged bracket. The shape of the notch is formed as an aperture of the diameter substantially equal to that of the flanged pin 19 and a segment cut out of the end of the arm to provide a pair of sloping surfaces leading from the outside of the end of the arm to the aperture, as shown in an enlarged side view of the end 20 of the arm 18 enclosed in a circle pointing to the end of that arm in FIG. 2. The hinge pin 19 of one bracket placed between those sloped surfaces easily forces the sloped surfaces apart to snap-fit the pin into the aperture. The two brackets thus snap-fit together to define an axis about which the plates 21,22 are hinged by the articulator 10.

Referring to FIG. 2, the vertex of each bracket 13,14 is defined by the ball 15 supported on an integrally cast stalk 16' in a position slightly offset from the center of the base 16 by half the width of the bracket arms as viewed in FIG. 2 so that when the brackets 13,14 are hinged together, as shown in FIG. 1, the balls 15 are centered in a plane perpendicular to the base of each and therefore perpendicular to the hinge axis for proper hinged movement of stone plates 21 and 22 relative to each other.

While each arm is reinforced at a right angle to the base of its bracket by a web in the corner as shown in FIGS. 1 and 2, the plastic arms themselves are sufficiently resilient to twist and bend slightly in order to allow the dental laboratory technician to not only gain access to the dental castings by pivoting one plate away from the other but to also check the occlusion of the teeth while the plates are closed together, during initial alignment of the bite and periodically thereafter to check the occlusion of prosthesis being modeled with the patient's teeth castings on the plates during the process of modeling prosthesis. The resilient flexibility of the bracket arms allows limited twisting and bending of the articulator bracket arms to allow motion of one plate relative to the other, thus grinding teeth of the two castings with occlusal tape between them to check the occlusion of the prosthesis being modeled with it in place.

Figure 3:
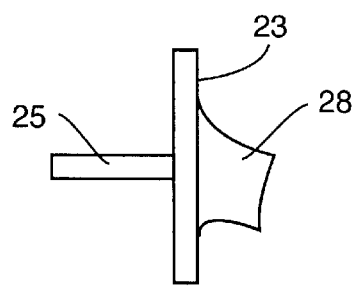
FIG. 3 is a side view of means for mounting the novel friction C-clamp utilized to form a ball-and-socket joint in accordance with the present invention to stone plates bearing castings of a patient's teeth as shown in FIG. 1, namely a plate with a perpendicular tab.

The sockets for the ball-and-socket joints 11,12 are preferably molded, like the brackets, in plastic as an integral part of mounting plates 23,24, one of which (plate 23) is shown in an end view in FIG. 3 in order to show a tab 25 perpendicular to the rear face of a mounting plate 23. That tab 25 is inserted into a slot 27 in the rear face of the casting plate 21 while an identical tab protruding from the rear face of the mounting plate 24 is inserted into a slot 26 in the rear face of the plate 22, as shown in FIG. 1. This is normally done with the teeth of the plate 21 aligned for proper bite over the teeth of the plate 22 after the balls have been snap-fit into the sockets of the ball-and-socket joints 11,12 with the balls free to turn in their sockets. After the tabs of the mounting plates are affixed in their slots using cynacrolate glue, and alignment of the plates are checked for occlusal of the dental castings, the C-clamp socket of joints 11,12 are tightened to affix the balls in their sockets to complete the alignment, as will be described in more detail below with reference to FIGS. 4 and 5. Any readjustments required for this alignment in the normal course of modeling prosthesis can be readily made by loosening the C-clamp socket joints and then retightening them.

Details of the improved sockets for these ball-and-socket joints 11,12 will now be described with reference to FIG. 4 which shows in a plan view a socket having a stalk 28 molded as an integral part of the mounting means illustrated in FIG. 3 for one of the ball-and-socket joints comprising a cylindrical body 29, as shown in FIG. 5. That cylindrical body has a doubly truncated, spherical cavity 30 of a radius substantially equal to the radius of a bracket ball 15. The circumference of that doubly truncated spherical cavity 30 is indicated in FIG. 4 by a dashed line. It is truncated at one end (the near end in FIG. 4, hereinafter referred to as the front end) a predetermined distance from the center of the spherically shaped cavity, thus providing the opening 31 into the cavity 30 through which a ball is snap-fit into place. That opening 31 is represented by a solid line in FIG. 4. A smaller opening 32 at the far end of the truncated cylinder, also represented by a solid line in FIG. 4, completes the formation of the C-clamp socket of a ball-and-socket joint once a radial gap 33 is formed in the cylindrical body 29. The result is a truncated spherical cavity forming a concave band, sometimes referred to herein as a concave C-clamp, to serve as a socket. Flanges 34 and 35 are formed as integral parts of the C-clamp at its free ends with a gap 33 extending through the flanges into the cavity 30, thus providing a concave C-clamp the free ends of which each have a separate flange with a gap between the flanges. One flange 34 is perforated to pass a threaded end of a bolt 36 to the other flange 35 adapted to receive the bolt in a threaded insert 37.

To insert the ball 15 into the socket through the opening 31 at the front side of the cylindrical body 29, the ball is pressed against the opening while the bolt 36 is partially or completely withdrawn so that the gap between the C-clamp flanges may spread to allow the ball to be snap-fit into place. To facilitate that, the front end of the cylindrical body 29 is preferably formed with a truncated conical surface 38, as shown in FIG. 5 to provide an inwardly sloping surface from the front of the body 29 to the opening 31 (represented by a solid circle line in FIG. 4) of the cavity 30 as shown in FIG. 5. The opening 32 at the far end of the cavity (represented in FIG. 4 by a solid line circle of smaller diameter than the front opening 31) will readily hold the ball in the cavity as the C-clamp springs back to restore the gap to its normal dimension after the ball is snap-fit into place, whereupon the bolt 36 is tightened to affix the ball in the C-clamp socket by the force of friction.

The knurled knob of the bolt 36 is large enough in diameter to allow tightening the bolt sufficiently to affix the ball in the C-clamp socket, but for even greater torque the knurled knob of the bolt is provided with a hexagonal socket for use with an Allen wrench. The stalk 28 supporting the C-clamp socket on the mounting plate 23 is angled so that the front opening 31 of the C-clamp socket is positioned at a convenient angle (about 22°) away from the mounting plate for accessibility of the bolt 26 to the technician using only his fingers for tightening.

Because the concave band C-clamp for the ball-and-socket joint is preferably made of plastic, as are the brackets of the articulator, an internally threaded metal insert 37 is pressed into a countersunk hole in the flange 35. The end of the countersunk hole that receives the threaded end of the bolt first is of a diameter to receive the small diameter end of the insert 37, and the other part of the countersunk hole is of a larger diameter to receive the greater diameter part of the insert 37, the shoulder of which allows torque to be applied to the bolt without causing the insert to rise toward the bolt head. To assure that the insert does not turn in the countersunk hole as torque is applied, that part of the insert of greater diameter is preferably provided with splines or other protuberances that bite into the wall of the countersunk hole as the insert is inserted so that it cannot turn in the countersunk hole. The small diameter end of the insert is preferably rimmed with a ridge so that as the insert is pressed into the hole, the ridged end will emerge in the gap 33 on the surface of the resilient plastic to prevent it from backing out while the bolt is being inserted for engagement with the insert.

The bolt 36 itself is provided with a flange 40 near the head thereof so that, as the threaded bolt engages the threaded metal insert 37 and is torqued to reduce the gap 33, the knurled head cannot advance to the socket flange 34, thus assuring finger space to hand turn the bolt.

To release the ball in the C-clamp socket the bolt is turned in the opposite direction, but in order to be able to quickly release and then reaffix the ball in the C-clamp a pivotal cam (not shown) can be used to apply the pressure on the C-clamp flange 35. In that case, the threaded insert 37 for the bolt is instead provided with an internally threaded cylindrical "nut" outside the flange 35 to serve as a pivot pin for the cam with its axis perpendicular to the bolt axis for receiving the threaded end of the bolt in an internally threaded perforation. The pivot pin then serves to hold the pivotal cam which, when hand turned 90° to 100° by a cam lever away from the cylindrical body of the C-clamp socket, pressure of the cam against the flange 35 is decreased and the gap between the flanges 34 and 35 is restored.

Referring to FIG. 6, the second embodiment of the present invention comprises a socket 41 in the form of a truncated spherical cavity supported on a bent stalk 42 cast integral with a mounting plate 43 having a tab 44 perpendicular to the plate for mounting the socket on the back of a stone plate bearing dental castings. The axis of the opening to the cavity of the socket 41 is at an angle of about 22° to the plate to facilitate inserting a bracket ball 45 of a pair of hinged brackets at an angle to the mounting plate, as shown in FIG. 1.

The direction of the angle for the opening of the cavity is selected so that the bracket ball 45 fitted into the cavity of the socket 41 will be at an angle of about 158° with respect to the surface of a stone plate bearing the teeth in a manner similar to that shown in FIG. 1 for the first embodiment.

The ball 45 is cast with equal perpendicular gaps that divide the ball into four equal parts, as shown in a top view of the ball adjacent to FIG. 5. The ball is cast integral with an articulator bracket 46 on a stalk 47 on top of the base 48 of the bracket. The stalk itself is thin and shown by itself in a plan view adjacent to FIG. 5 shaped like a washer.

The diameter of the ball is substantially equal to the internal diameter of the cavity 41. The opening of the cavity for the ball 45 is, of course, smaller than the diameter of the ball, but the ball may be readily snap-fit into the socket cavity because the gaps between the four equal parts of the ball allow the parts of the ball (connected together through the stalk 47 to the bracket bore 46) to bend at their connections toward each other, thus effectively allowing the ball to decrease in size as it is inserted into the socket cavity.

Once the ball 45 is snap-fit into the socket cavity 41, a screw or bolt 50 with a conical point is turned in a threaded perforation through the base of the bracket base 48 and stalk 47 thereby advancing the tip of the bolt into the space between the four parts of the ball to spread them apart against the wall of the socket cavity. The core diameter of the bolt is approximately equal to the dimensions of the gaps, but the diameter of the threads on the bolt is slightly greater so that, as the point of the bolt is advanced, the four parts of the ball are tightly pressed against the cavity wall.

Although particular embodiments of the invention have been described and illustrated herein, it is recognized that modifications may readily occur to those skilled in the art. Consequently, it is intended that the claims be interpreted to cover such modifications and equivalents thereof.

What is claimed is:

1. In a dental model articulator having a pair of U-shaped brackets hinged together at both ends of each bracket and each bracket having a ball between ends thereof for forming a ball-and-socket joint connection to a separate one of two stone plates bearing separate ones of a pair of a patient's dental castings used during a process for modeling of prosthesis to fit with said patient's teeth, each ball-and-socket joint having a doubly truncated spherical cavity socket affixed to a separate stone plate and having a concave band surface of a width less than said ball's diameter and a radius of curvature substantially equal to said ball's radius for capturing said ball upon pressfitting said ball through an opening on one side where said spherical cavity is truncated close to the center of said spherical cavity to allow said ball to be press fitted through the opening created by truncating the sphere on said one side, an improvement comprising releasable means for affixing said ball in said socket by frictional force alone between said socket and said ball, said releasable means operable to effectively adjust a radius of one relative to the other of said ball and said concave band surface, thereby to increase said frictional force between said ball and said concave band socket for affixing said ball in said socket, whereby alignment of said two plates achieved through adjustment of relative position of said ball in said socket of each ball-and-socket joint is maintained until said mechanically releasable means is released for realignment of said ball in said concave band socket as necessary during said process for modeling of prosthesis.

2. An improvement as defined in claim 1 wherein said concave band socket comprises a C-clamp having a concave band with a gap, a first flange at a first end of said band at said gap, and a second flange at a second end of said band at said gap, said concave band forming a doubly truncated spherical cavity with a diameter substantially equal to a diameter of said ball, said doubly truncated spherical cavity having one opening at one truncated side and a second opening on an opposite truncated side, said opening on said one side having a diameter less than said diameter of said ball, thus requiring said ball to be press-fitted into said doubly truncated spherical cavity by forcing said gap between said flanges to spread, thereby allowing said opening on said one side of said truncated spherical cavity to expand under pressure of said ball to allow said ball to pass into said truncated cavity while said second opening on said opposite truncated side having a diameter less than said diameter of said ball captures said ball in said cavity, and a bolt through said flanges for reducing said gap in said concave-band C-clamp between said first and second flanges to secure said ball in said truncated spherical cavity under tension around said ball, whereby said releasable means affixing said ball-and-socket joint is achieved by turning said bolt in an opposite direction.

3. An improvement as defined in claim 1 wherein said concave band socket comprises a truncated cavity of a diameter substantially equal to a diameter of said ball, and said means for affixing each ball in a respective ball-and-socket joint comprises a stalk supporting said ball on a base between ends of said bracket, and a threaded perforation through said stalk to said ball, said ball having mutually perpendicular gaps that divide said ball into four equal parts, such that four corners of said four equal parts are equally spaced from an extended axis of said threaded perforation, and a bolt having a conical tip and a core diameter substantially equal to space between diametrically opposite corners of said four parts of said ball, and threads on said core that engage said threaded perforation of said base and said stalk and bear against said corners of said four parts of said ball whereby, upon further turning said bolt in said threaded perforation to advance said bolt into said space between said corners of said four ball parts, said four parts are spread apart more and more by said bolt as its conical tip advances through said threaded perforation and into said ball, thereby pressing said four parts against said cavity wall to produce a force of friction of said ball against said cavity to releasably affix said ball in said cavity.

* * * * *